United States Patent
Saalasti et al.

(10) Patent No.: US 7,192,401 B2
(45) Date of Patent: Mar. 20, 2007

(54) METHOD FOR MONITORING ACCUMULATED BODY FATIGUE FOR DETERMINING RECOVERY DURING EXERCISE OR ACTIVITY

(75) Inventors: Sami Saalasti, Jyväskylä (FI); Joni Kettunen, Säynätsalo (FI); Aki Pulkkinen, Palokka (FI); Heikki Rusko, Muurame (FI)

(73) Assignee: Firstbeat Technologies Oy, Jyvaskyla (FI)

( * ) Notice: Subject to any disclaimer, the term of this patent is extended or adjusted under 35 U.S.C. 154(b) by 87 days.

(21) Appl. No.: 10/523,156

(22) PCT Filed: Aug. 18, 2003

(86) PCT No.: PCT/FI03/00607

§ 371 (c)(1),
(2), (4) Date: Jan. 27, 2005

(87) PCT Pub. No.: WO2004/016173

PCT Pub. Date: Feb. 26, 2004

(65) Prior Publication Data

US 2006/0032315 A1    Feb. 16, 2006

(30) Foreign Application Priority Data

Aug. 16, 2002 (FI) .................................. 20025038

(51) Int. Cl.
*A61B 5/02* (2006.01)
*A61B 5/04* (2006.01)
*A61B 5/00* (2006.01)

(52) U.S. Cl. ............... 600/500; 600/483; 600/481; 600/509; 600/300

(58) Field of Classification Search ................ 600/547, 600/587, 481, 483, 500–503, 508, 509, 300, 600/301, 529–543
See application file for complete search history.

(56) References Cited

U.S. PATENT DOCUMENTS

| 4,883,063 A | 11/1989 | Bernard et al. |
| 5,891,044 A | 4/1999 | Golosarsky et al. |
| 6,104,947 A | 8/2000 | Heikkila et al. |

(Continued)

OTHER PUBLICATIONS

Keyser, R.E. et al. "Oxygen uptake during peak graded exercise and single-stage fatigue tests of wheelchair propulsion in manual wheelchair users and the able-bodied". Archives of Physical Medicine and Rehabilitation, Oct. 1999, vol. 80, No. 10, pp. 1288-1292. (abstract) MEDLINE on line} [retrieved on Oct. 23, 2003 ]. Retrieved fro MEDLINE, Accession nr: 10527089, ISSN 0003-9993.

(Continued)

*Primary Examiner*—Robert L. Nasser
*Assistant Examiner*—Navin Natnithithadha
(74) *Attorney, Agent, or Firm*—Fildes & Outland, P.C.

(57) ABSTRACT

The invention relates to a method for determining accumulated body fatigue index (BFI), wherein one or more parameters from the measurement of one or more signals are obtained sequentially as input and these parameters are information on the intensity of physical activity. BFI has a predetermined initial value, and next BFI value is always a sum of BFI-value and a difference. The difference is combination of upslope and optional downslope components of BFI determined with the said parameters and the upslope component and the optional downslope component are each determined with a function, which is scaled by a preset physiological character.

17 Claims, 9 Drawing Sheets

U.S. PATENT DOCUMENTS

| | | |
|---|---|---|
| 6,516,222 B2 * | 2/2003 | Fukuda ........................ 600/547 |
| 7,065,399 B2 * | 6/2006 | Nakada ........................ 600/547 |
| 2004/0092840 A1 * | 5/2004 | Nakada ........................ 600/547 |

OTHER PUBLICATIONS

DeMarie, S. et al. "V02 slow component correlates with vastus lateralis de-oxygenation and blood lactate accumulation during running". The Journal of Sports Medicine and Physical Fitness, Dec. 2001, vol. 41, No. 4, pp. 448-455. (abstract) MEDLINE [on line] [retrieved on Oct. 23, 2003] Retrieved from MEDLINE, Accession nr: 11687763, ISSN 0022-4707.

Tench, C. et al. "Aerobic fitness, fatigue, and physical disability in systemic lupus erythematosus". Journal of Rheumatology, Mar. 2002, vol. 29, No. 3, pp. 474-481. (abstract) BIOSIS [on line] [retrieved on Oct. 23, 2003]. Retrieved from BIOSIS, accession nr: 200200253562, ISSN 0315-162.

Crumton-Young, L. et al. "The Total Body Fatigue Estimator". UCF/IEMS, Current Research Projects [on line], Nov. 1, 2002 [retrieved on Oct. 22, 2003], pp. 1-3. Retrieved from the Internet:<URL:http://www.iems.ucf.edu/ver40/about/research.htm>, see p. 3, abstract.

* cited by examiner

METHOD FOR MONITORING ACCUMULATED BODY FATIGUE FOR DETERMINING RECOVERY DURING EXERCISE OR ACTIVITY

BACKGROUND OF THE INVENTION

1. Field of the Invention

The present invention relates to a method for deriving information on exercise and physical activity induced changes in body fatigue, wherein parameters from the measurement of a physiological signal are obtained as input and these parameters being information on the intensity of exercise or physical activity. More generally speaking the invention relates to the monitoring of body functions, in particular to methods that are aimed to describe exercise and physical activity. The invention relates also to a method for deriving predictions on body fatigue and recovery during physical exercise and while recovering from such exercise. The term "body fatigue" means here also its counterpart, homeostatic disturbance induced by physical activity.

The current invention presents a procedure for predicting body fatigue during exercise and recovery from exercise on the basis of physiological measurement.

2. Description of the Prior Art

The control of exercise intensity, duration, and information from fatigue and recovery from the exercise are key elements in maintaining and achieving a good physical fitness and especially important in health enhancing physical activity, wherein exercise is directed to improve health and fitness. In particular, for individuals that suffer from some clinical condition, such as cardio-vascular disease, it is extremely important to maintain physical activity within safe limits. In athletic sports, disturbance of homeostasis induced by training exercises is also important for attaining a training effect.

The accumulation and reduction of the effects of exercise on the body is described in this document by two related concepts, body fatigue and recovery. Body fatigue is defined as a decrease of physiological resources due to the effects of exercise and physical activity. Recovery from physical exercise is defined as the restoration of physiological resources that has been used during the accumulation of body fatigue during exercise.

It has been generally accepted that especially the balance between exercise and recovery is important in athletic training and sports. Optimal training requires a disturbance of homeostasis and enough rest to recover from the exercise. This may be a hard goal to achieve for a person engaged in physical exercise and training, since exercise methods are mainly based on experience and general knowledge on the physiology. If exercise bouts are too mild, no positive training effect occurs because disturbance to the homeostasis has been minimal. On the other hand, if exercise bouts are scheduled too severe and too frequent, negative training effect may occur because bodily functions have not been restored properly. To gain positive training effect exercise bouts must be scheduled optimally, in order to give the body a chance to adapt a new level of functioning.

To summarize, a method that would give feedback on body fatigue and time required for recovery on the basis of individual's own physiological characteristics and responses to exercise would be certainly helpful to many individuals engaged in health enhancing physical exercise and fitness training and would potentiate more optimal and safe training schedules.

Oxygen consumption ($VO_2$), that is, the rate of oxygen intake, is a central mechanism in exercise and provides a measure to describe the intensity of the exercise. Oxygen is needed in the body to oxidize the nutrition substrates to energy and therefore $VO_2$ is very tightly coupled with the energy consumption requirements triggered by exercise and physical activity. American College of Sports Medicine Position Stand recommendations for exercise prescription (ACSM 1998) suggests the use of $VO_2$ for the measurement of physical activity.

The level of oxygen consumption can be measured by different methods. The most accurate methods rely on the measurement of heat production or analysis of respiratory gases but require heavy measuring equipment and are therefore restricted to the laboratory environment. There are also more cost effective and practical means to estimate oxygen consumption using indirect methods based on the measurement of, for example, heart rate, ventilation, skin temperature, or movement. In particular, there is a close relationship between heart rate and oxygen consumption during exercise as increased oxygen consumption in the muscles requires an increase in circulatory volume. Heart rate is a major determinant of the circulatory volume and often provides a reasonable estimate of the oxygen consumption.

Maximal oxygen consumption ($VO_{2max}$) is defined as the maximal rate of oxygen intake during exhaustive exercise and denotes person's ultimate capacity for aerobic energy production. Usually this is achieved by stepwise exercise protocol to a voluntary exhaustion (maximal exercise stress test), during which the oxygen uptake is measured. Also non-exercise methods are available to estimate person's $VO_{2max}$ based on individual characteristics such as, for example, age, sex, anthropometric information, history of physical activity, or resting level physiological measurements (e.g. Jackson et al. 1990).

Knowing the absolute oxygen consumption rate at which a person is exercising and the maximal attainable oxygen consumption of the same person, exercise intensity can be described as a percentage of the maximum This is crucial, as maximal values of $VO_2$ can vary markedly between subjects. Thus, two persons that differ in their maximal $VO_2$ but exercise at the same relative intensity have similar exercise impact on their bodies.

Athletic training and physical exercise in general has acute effects on body resources and body fatigue. The accumulation of body fatigue is depends on and determined by the characteristics of the exercise, including intensity, duration, and phase of the exercise. At high exercise intensities the energy requirements increase and induce a proportional reduction of available body resources. The mobilization of body resources is associated with accelerated physiological function and involves increased levels of oxygen consumption, circulation, ventilation, and hormone secretion (e.g., catecholamines). Metabolic function during exercise is characterized by increased rate of energy release from carbohydrates and body fats, and involve also by-products such as lactate, all of which reduce the level of metabolic resources available in the body.

The physiological processes of recovery from exercise involve a renewal of consumed body resources and are generally characterized as opposite to those during exercise. The level of physiological function shows attenuation towards normal levels. The recovery of metabolic resources involves replenishment of energy stores (e.g., glycogen) and removal of exercise-induced by-products (e.g., lactate). The process of recovery requires oxygen and therefore $VO_2$ and heart rate remain elevated after exercise and may be used as composite indicators of the replenishment of the resources in the body. This indicates that the extend of exercise induced fatigue may be determined by the characteristics of the recovery process after the exercise.

The prior art has also documented some work on the measurement of exercise levels and stress on the basis of heart rate variability (HRV). HRV denotes the extent of rhythmic changes evident in the heart rate. The relationship of the heart rate variability to the exercise and stress is well known and documented in the prior art. Golosarsky and Wood (U.S. Pat. No. 5,891,044), Heikkilä and Pietilä (U.S. Pat. No. 6,104,947), and Hoover (U.S. Pat. No. 6,212,427) have all implemented a technique of determining the stress caused by exercise using different types of indices based on HRV. These methods usually require preset individual thresholds and state declarations, as defined by the user or history values, to give an estimate of the level of stress caused by the exercise and workload. The described methods are relatively simple, easy to implement and provide feedback on the acute exercise load.

It has been shown earlier that the amplitude of the HRV is associated with the intensity of physical activity. It is also known that HRV is associated with the aerobic threshold of the metabolism, which usually occurs at approximately 50–75% of maximal intensity in exercise (Tulppo et al., 1996). It is therefore clear to anyone experienced in the art that the HRV is primarily a measure of the intensity of the exercise and therefore provides little if any information on the dynamic phenomena of accumulation of body fatigue during different phases of the exercise. Thus, the described measures are primarily dependent on the instantaneous characteristics of the exercise and are not capable of adapting to temporal dynamics in different phases of the exercise. For example, during a short but intensive exercise HRV reflects high stress than considerably longer exercise with lower intensity, although in this case the longer duration exercise could accumulate, in effect, higher levels of body fatigue and a longer time required for recovery.

Prior art has documented work on deriving information on the accumulation of body fatigue and exhaustion as due to physical workload. Bernard, Sherwin, Kenney, William and Lewis (U.S. Pat. No. 4,883,063) have presented a method for monitoring heat stress, as especially occurring in a hot factory environment. The levels of heart rate and skin temperature are used within predefined temporal window to monitor potential exhaustion and a warning is triggered if a predefined threshold value is passed. The solution also includes an assessment of recovery on the basis of heart rate measurement, during which the person has to stay at rest for few minutes.

It is apparent to one skilled in the art that the method of Bernard et al. is designed for the analysis of tonic workload with known properties (e.g., heat stress). In most real life occasions, intensity of the exercise may vary markedly with different phases of the exercise due to, for example, conditions (e.g., up- and down hills), training mode (walking and running), or any means of controlling exercise intensity due to, for example, sports characteristics, physiological state or training protocol. The method of Bernard et al. is dependent on the instantaneous levels of the heart rate and skin temperature and therefore, in a similar manner to the methods based on HRV, does not include history information on the accumulation of body fatigue. The method may provide reliable results within constant working environment with known workload, but it is clearly not sufficient for monitoring body fatigue during exercise, wherein the level of heart rate is heavily dependent on the intensity of the exercise and thus does not indicate level of exhaustion.

The method presented by Bernard et al. has also some limitations with regards to the monitoring of recovery. The estimation of the recovery is somewhat problematic in the described method, since it requires few minutes of rest and is not therefore applicable to continuous monitoring of recovery within dynamic changes in exercise phases and intensities. In general, the method does not involve a differential estimation of the recovery component, which impairs the estimation of the recovery during dynamic exercise, wherein a decrease in exercise intensity may induce a reduction in recovery state. All this implies that the described method is not capable of producing continuous information on recovery and does not predict the amount of recovery required in advance to the onset of actual recovery.

To summarize, the monitoring of exercise effects on the body is not possible with a model that does not take into account the fact that exercise has a cumulative impact in the accumulation of the body fatigue and that it is not equal at different intensities and phases of the exercise. The description of the prior art clearly indicates that the described methods are highly dependent on the exercise state and do not contain cumulative information on the accumulation of fatigue through the exercise. The described methods neither do potentiate a continuous monitoring of recovery, which would be most important in any condition wherein the exercise is dynamic and the user would benefit from the information on the onset and progress of recovery.

OBJECTS AND SUMMARY OF THE INVENTION

The object of the present invention is to provide new types of methods and apparatuses for monitoring and controlling the processes body fatigue and recovery of persons engaged in fitness training and physical exercise. The characteristic features of the invention are disclosed in the accompanying Claims. According to the preferred embodiments, the innovation potentiates the monitoring of the body fatigue during exercise and recovery from exercise without the need for any external professional aid. The invented procedure is based on the measurement of one or more physiological parameters that describe the intensity of the exercise, such as heart beat, movement, ventilation, skin temperature, energy consumption, or oxygen consumption.

The innovation offers a method of tracking continuously the influence of exercise on body fatigue and recovery from exercise without the need of restricting to laboratory environment or equipments. The procedure can be used to provide real time feedback on exercise status and body fatigue to optimize physical exercise, sports training and recovery, and to provide predictions of time to become exhausted during exercise and time requirements for body recovery.

The present innovation includes several features that clearly differentiate it from the prior art and provide new benefits for the user. (1) The formation of the body fatigue index (BFI) is based on a set-up wherein the actual extent of recovery time required following the exercise are used to determine the properties and dynamics of the accumulation of the body fatigue effect. (2) Given that the physiological determinants of the body fatigue may be measured only after exercise while recovering, the present procedure predicts the expected recovery requirements already during the exercise, in advance to the actual recovery after the exercise. (3) After exercise, the comparison of the actual monitoring of recovery with the predictions based on BFI provides information on the progress of the recovery process. (4) The procedure is capable of including accumulative information on the past and is not a simple state measure of exercise stress, which potentiates the use of the procedure in tracking exercise effects during exercise with dynamic shifts in intensity and duration.

The computational part of the exercise-phase dependent accumulation of BFI, as solved in the present innovation, may be generally described with the following functional notation, $$BFI_{t+1}=BFI_t+f(BFI_t, \text{exercise\_intensity}_t, \Delta t)$$

wherein the recursive implementation of the accumulation of the BFI has the benefit of not having requirements for knowing a priori the beginning time of the exercise and different durations of exercise at varying intensities. As with other solutions, wherein the increment in the body stress is dependent on the instantaneous characteristics of the exercise, as derived from, for example, measured or estimated oxygen consumption or heart rate, the present solution contains inherently history information on the exercise and is capable of adapting to dynamic changes in exercise intensity with different phases of the exercise. $\Delta t$ denotes the time difference between consecutive sampling points.

Accumulated body fatigue index (BFI) is determined in a manner, wherein one or more parameters from the measurement of one or more signals are obtained sequentially (typically 1–60 s) as input and these parameters being information on the intensity of physical activity. BFI has a predetermined initial value (e.g. zero), next BFI value is always a sum of BFI-value and a difference, and the difference is combination of upslope and optional downslope components of BFI determined with the said parameters. The upslope component and the optional downslope component are each determined with a function, which is scaled by a preset physiological character. Most preferably these functions are independent from the duration of the physical activity, which means that both components give the new difference without information about the duration of physical activity. In the calculation instead of BFI may be used an intermediate measure reflecting accumulative physical activity, which is then transferred to BFI-value.

A reader with experience in the art may easily perceive that the level of sophistication and function in the present innovation is advanced to the prior art and that the present innovation involves several features that are clearly distinguishable. In particular, the present innovation is not being based on direct monitoring of measures related to exercise state, such as heart rate variability.

The invention may be applied to and in association with devices such as heart rate monitors and other mobile or wearable computing devices, fitness equipments, and software, wherein there is the capability to receive information on one or more physiological measures, such as oxygen consumption, heart beat, skin temperature, or respiratory activity. This procedure may also be highly useful in the context of the ambulatory ECG and heart beat analysis systems wherein it is of importance to detect whether the source of increased heart rate is based on exercise and physical activity induced effects on the body or due to other source that has an accelerative effect on the cardiovascular system.

DETAILED DESCRIPTION OF THE PREFERRED EMBODIMENTS

Figure 1A:
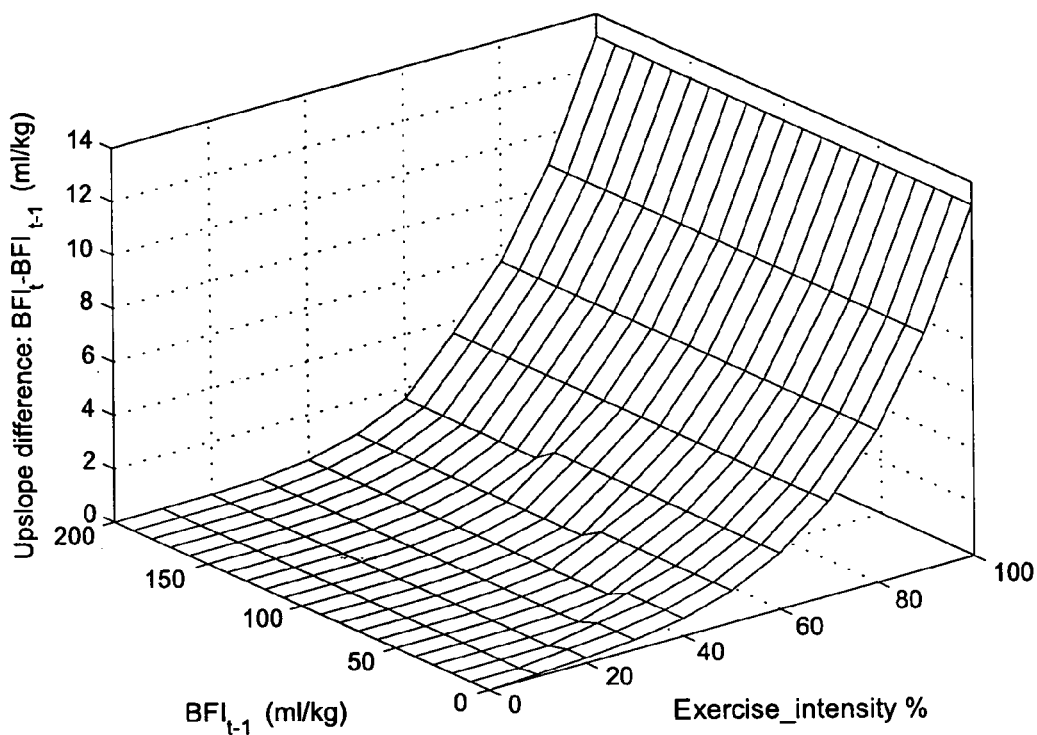
FIG. 1a. An example of the upslope component of the BFI as a function of previous level of accumulated BFI and exercise intensity.

The innovation is described here with the aid of an example implementation. It should be noted that the described system is not bound to any specific model or specifications, but rather, different alterations, forms, and improvements are possible and are in line with the spirit of the innovation. Thus, the following merely contains a description of the preferred embodiments of the innovation.

The preferred embodiment applies oxygen consumption as the input physiological measure. Given the relative difficulty in measuring oxygen consumption directly, the level of $VO_2$ is estimated on the basis of heart beat, for example, by applying a polynomial equation or a more complex function relating heart beat level to the level of $VO_2$. However, it is important to notice that whereas the $VO_2$ is used here to index exercise intensity, also other measures, such as heart beat level, respiratory interval and ventilation, skin temperature, energy consumption, and movement and acceleration, may be used directly without any transformation to $VO_2$ to estimate exercise intensity and physical activity, or may be used indirectly by using a transfer function to estimate $VO_2$ or other quantity that relates to the intensity of physical activity. One possible embodiment would derive information on the intensity of physical activity from physical workload, such as that obtained from fitness equipment or from information on distance, speed, or altitude changes during workout, for example. It is also of note that the required input signal in physical activity levels may also be a combination of two or more signals. Such a case would be preferred for example, in terms of fitness equipments wherein it would be useful to use information on both heart rate and physical workload to derive reliable index of the level of physical activity.

The input value of the VO₂ is presented as proportional to the maximum in the illustrated example of the preferred embodiment of the innovation; it should be, however, clear to anyone experienced in the art that the scope of the present innovation does not in any manner limit the use of any of the input measures or derived measures in either absolute values, or as proportional to maximum, minimum, or both maximum and minimum (so called reserve) values. Different scaling options should be considered to gain optimal results when applying the present innovation in different contexts. The optional maximum or minimum values may be either inputted by the user, may be preset, or may be derived from the existing user data.

In this innovation, the scale and measurement of body fatigue index (BFI) is performed through the estimation of the level of recovery demands after exercise. The preferred embodiment described here uses the magnitude of the VO₂ that is in excess to the acute body demands determined by the level of physical activity as an index of body fatigue. This is based on the notation that the extent of recovery processes to be carried out in order to return to the normal homeostasis of the body and therefore the extent of BFI are reflected in the quantity of excessive VO₂ consumption after the exercise. Another preferred or alternative methods of estimating the extent of recovery demands would consist of determining the extent of additional heart rate or heart rate variability level when compared to baseline, or lactate levels during or after the exercise. In addition to increased oxygen consumption, increased heart rate level, decreased heart rate variability and increased lactate concentration, there may be other indices forming a scale to the recovery demands as well, such as glycogen concentration, other metabolic or hormonal indices, and self-reported levels of perceived exertion.

It is important to understand that the purpose of using physiological measures of recovery is to provide preset values on the dynamics of bow body fatigue accumulates. In another words, these measures provide a scaling for the accumulation of BFI upon different duration, intensity, and phases of physical exercise. Thus, for example, the amount of increased oxygen consumption after exercise may be used to indicate the degree of body fatigue that is accumulated during the exercise. Nevertheless, as indicated above, the present innovation is not restricted to the above measures only, but rather, allows the use of other types of measures to index the amount of recovery demands after exercise.

Given that the measures of body fatigue and recovery can be monitored only after the exercise, when the actual recovery is in progress, poses a problem for the generation of feedback already during the exercise for a user engaged in exercise and physical training. The present innovation solves this problem by predicting the extent of recovery requirements already during the exercise, before the recovery has actually occurred, which allows to represent feedback on exercise status and body fatigue on a real-time basis. This procedure is based on an iterative model that predicts the post-exercise increase in the oxygen-consumption during the exercise. The iterative; real-time solution of predicting post-exercise increase in oxygen consumption may have been possible by fitting a recursive, real-time capable algorithm to the database consisting of recovery assessment in combination with different exercise intensities and durations.

Figure 4:
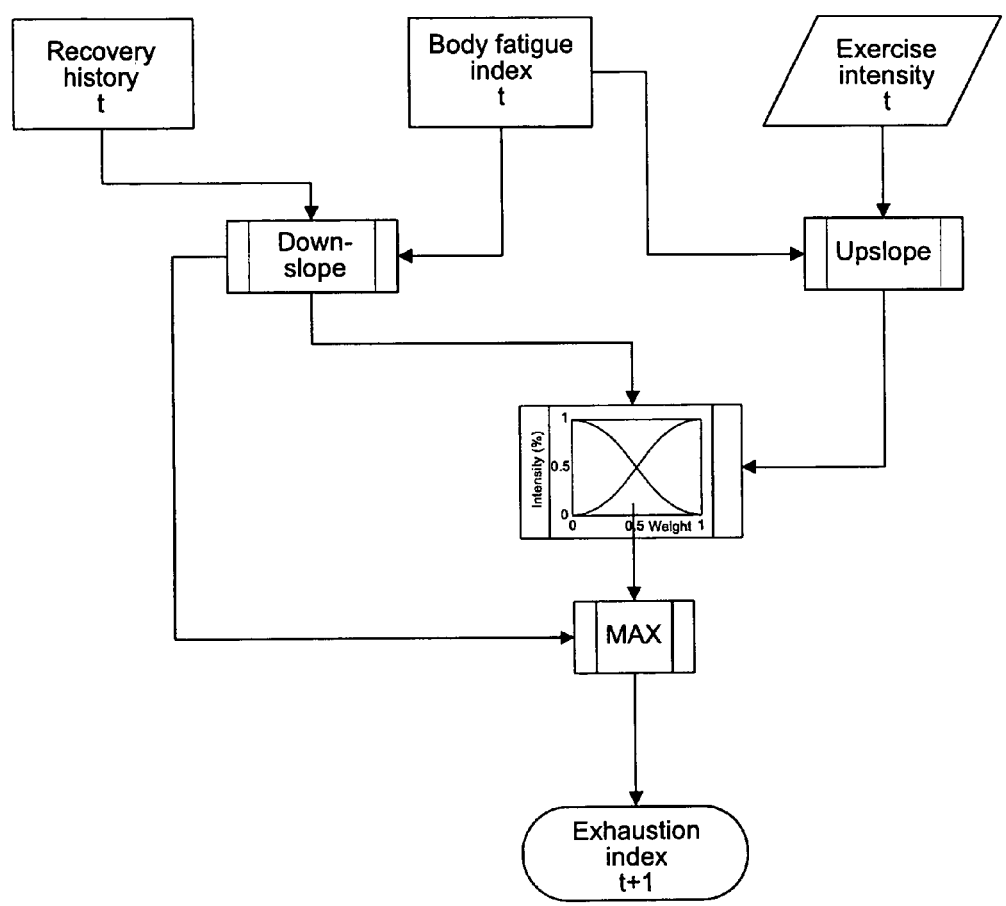
FIG. 4. A flowchart presenting the calculation of the BFI and explanation of flowchart symbols.

The BFI is formed in a recursive manner using the previous values of the BFI and the intensity of the exercise at the moment. The modeling of BFI and recovery is based on the computation of two components, an upslope component and a downslope component. FIG. 4 illustrates an overall view of the system.

$$\begin{cases} c_1 \cdot t + c_2, & t >= \dfrac{c_2}{(c_3 - c_1)} \\ c_3 \cdot t, & \text{else} \end{cases} \quad \text{Equation 1}$$

$$c_1 = b_1 \cdot \text{excerise\_intensity}_t^4$$

$$c_2 = b_2 \cdot \text{excerise\_intensity}_t$$

$$c_3 = c_1 + b_3 \cdot \text{excerise\_intensity}_t$$

$$b_i > 0, i = 1, 2, 3$$

$$y^{-1}(BFI_t) = \begin{cases} \dfrac{BFI_t - c_2}{c_1}, & \dfrac{BFI_t - c_2}{c_1} >= \dfrac{c_2}{(c_3 - c_1)} \\ \dfrac{BFI_t}{c_3}, & \text{else} \end{cases}$$

$$upslope(\Delta t, BFI_t) = \begin{cases} y(\Delta t + y^{-1}(BFI_t)), & BFI_t > 0 \\ y(\Delta t) & \text{else} \end{cases}$$

Figure 5:
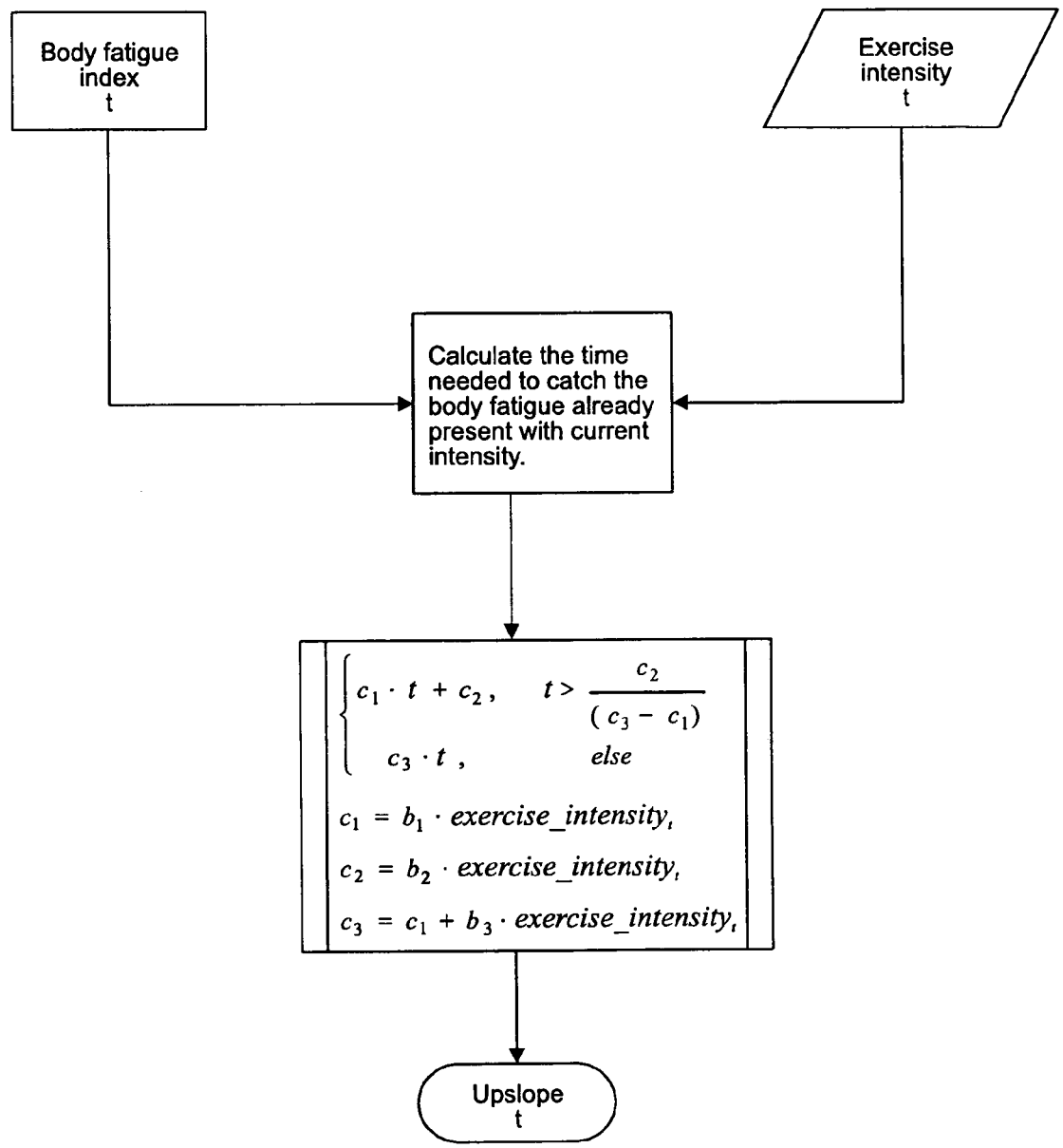
FIG. 5. The calculation of upslope component.

Equation 1 (FIG. 5) summarizes the calculation of the upslope component in this example. It is a composition of genuinely ascending piecewise linear function y and its inverse $y^{-1}$. Function y models the upslope as a function of former body fatigue index $BFI_t$, time difference between observations $\Delta t$ and exercise intensity at current time instant t. To model the BFI already cumulated in the system the inverse $y^{-1}$ solves the time needed to reach the former BFI level with current intensity. The addition (i.e., sum) of two time components, the time difference $\Delta t$ and $y^{-1}$ ($BFI_t$) is used to calculate the new upslope value with the function y. Time difference $\Delta t$ expresses the distance in minutes between the former and current BFI values.

Figure 1B:
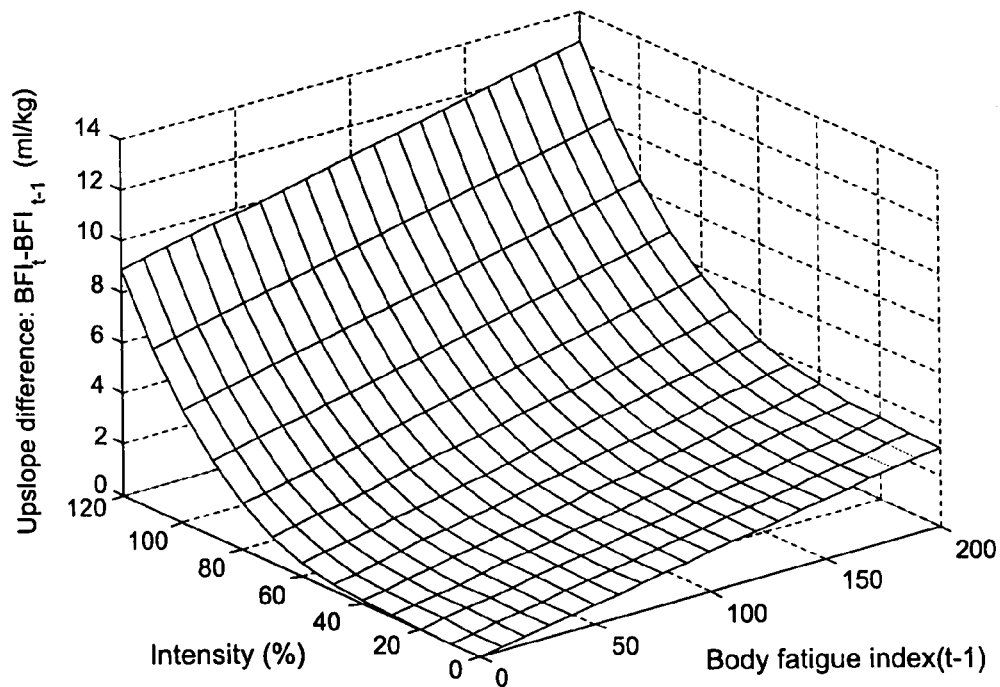
FIG. 1b. Another example of the upslope component of the BFI as a function of previous level of accumulated BFI and exercise intensity.

In this manner, the upslope component is capable of responding to the duration of exercise and past accumulation of body fatigue without forcing the model or user to classify the end and beginning of the exercise. The function relating exercise intensity and accumulated BFI to the up-slope (i.e., increasing) component of the BFI is illustrated in FIG. 1a. The intensity of the exercise is in proportional units (e.g., percents).More advanced functions would take account the accumulated value in addition to the exercise intensity in upslope difference, see FIG. 1b.

The specific implementation of the upslope is dependent on the scale of physiological quantity that it is being referred to. The degree to which the previous value of BFI is taken into account in the calculation of the upslope component is, in part, determined by the physiological conditions to which the scale of BFI is referred to. Accordingly, empirical characteristics of the physiological quantity that is being indexed by BFI may determine some of the properties of the upslope component of BFI.

There are several types of general implementations for the upslope. In this particular example and FIGS. 1a and 1b it is shown that the upslope may be presented as an accumulative difference (i.e., increase) from the previous data point. Another implementation would determine the next value of BFI directly on the basis of previous level of BFI and current physical intensity (not shown).

It is also of note here that the upslope component may be also preset to take into account different phases of the exercise, so that the implementation of the BFI would include information on state and exercise phase dependent physiological conditions. The decision to implement this information is, of course, dependent on the physiological quantity which scale is being determined. The unknown parameters of the example implementation of the upslope component presented in Equation 1 are solved with empirical data containing at least the intensity of the exercise, time and accumulated BFI in the end of the recording. The quality of the empirical data should be considered to have adequate scaling of the phenomena, i.e., exercises with different intensities and duration.

$$downslope(\Delta t) = \frac{1}{c^{\Delta t}}, \quad c > 1 \qquad \text{Equation 2}$$

Figure 2:
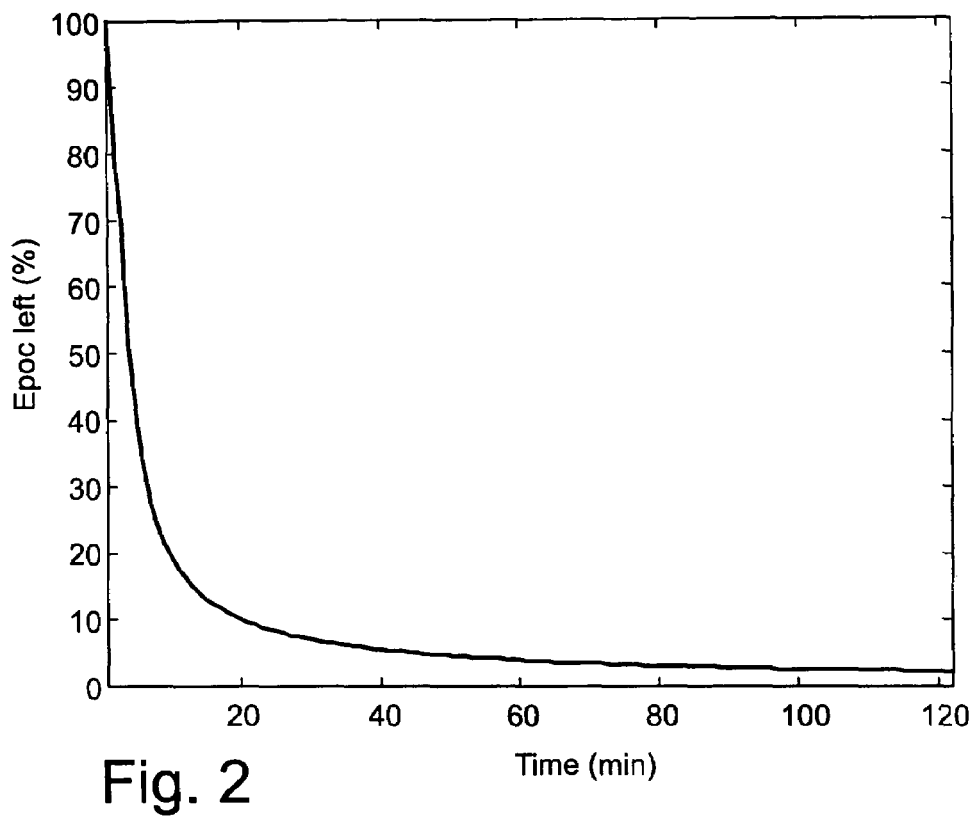
FIG. 2. The relationship between time in minutes and oxygen depth left in percents presented with an empirical data. The figure also includes a mathematical model estimated from the data.

The downslope component is a genuinely decreasing function of time. The function is based on the modeling of the recovery after physical exercise, wherein the progress of the recovery is determined by a physiological measurement, such as the increased rate of oxygen consumption after the exercise, as used in the example of the preferential embodiment. Other useful indices would be the extent of heart rate that is above rest or acute physical demands, decreased HRV, and lactates, the recovery of all of which components to resting levels is determined on the exercise characteristics and accumulated body fatigue. In the present embodiment the progress of the decrease in BFI is based on a proportional model of decrease as a function of recovery time, that is, the shape of the proportional recovery function is not affected by the quantity of BFI. Naturally, the downslope-component may be constructed alternatively as a more complex model, e.g., as a function of time, body fatigue or exercise intensity. FIG. 2 illustrates the model of the proportional recovery, which is based on the empirical data on the quantification of the rate of excessive oxygen consumption after the exercise.

The recovery is exponentially inversely proportional to time, i.e., at the beginning the progress of the recovery is the fastest.

Figure 6:
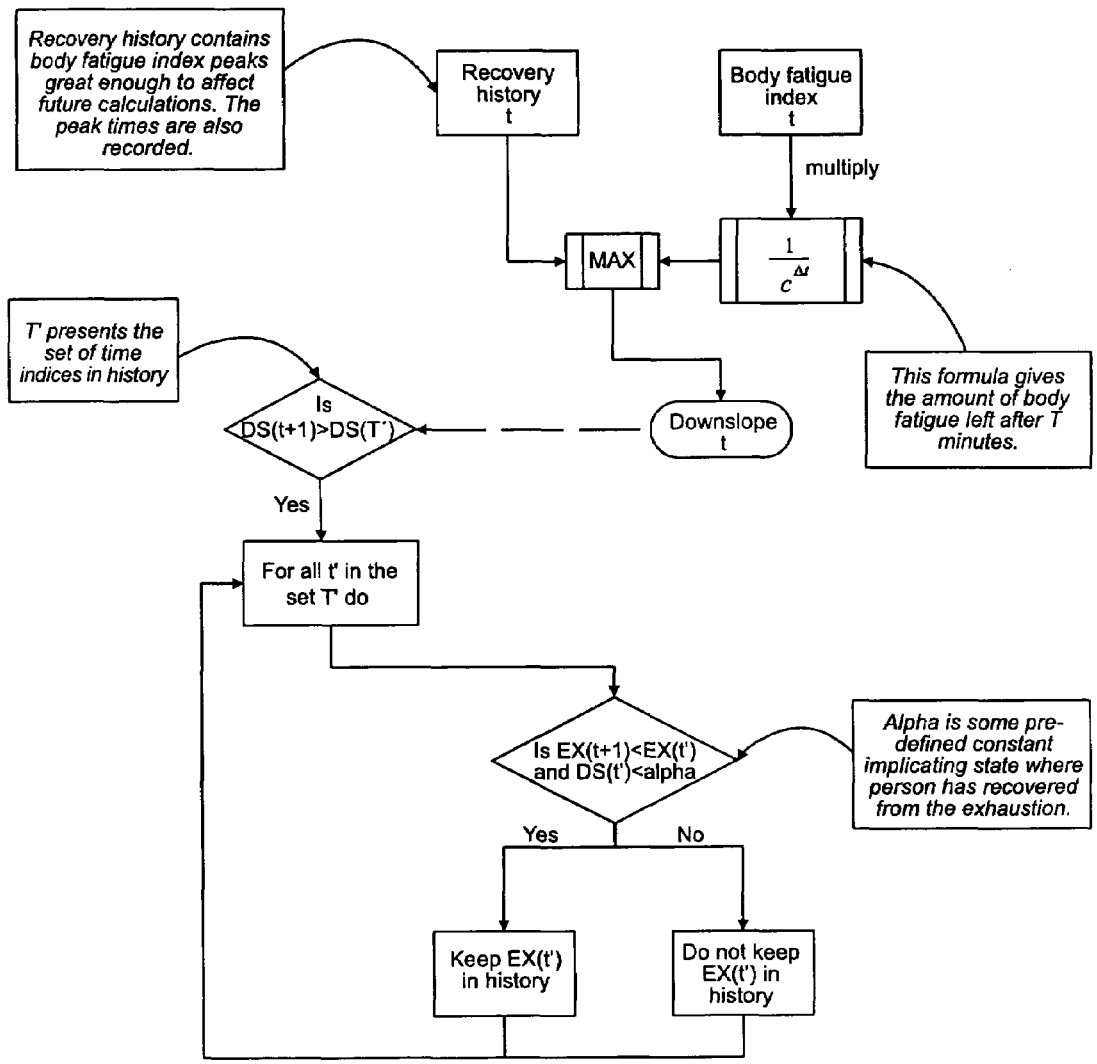
FIG. 6. The calculation of downslope component and recovery history.

An example implementation of the formulas and parameters of the downslope component are presented in Equation 2 and FIG. 6. In this case, the downslope is based on EPOC (i.e., excess post-exercise oxygen consumption, which is also often referred to as oxygen debt), the extent of physical activity induced heightened level of oxygen consumption after the cessation of physical activity, and it is clear that if the recovery of heart rate, heart rate variability, lactate, or other quantitative measure of recovery demands were used as a reference of formulating the downslope, the form of the equation would be substantially different. It is also evident to one skilled in the art that, in order to formulate optimal downslope function, the data that is used in the formation of the downslope component may be scaled according to preset criteria such as between 0 and 1, for example, to standardize the reference data-set.

Exercise and physical activity may consist of several periods of increased physical activity and following periods of recovery. These "exercise bouts" and periods of decreased physical activity may be described as separate components that each have their own recovery function (i.e., downslope) and which, when combined, form the total amount of BFI. In this manner, the characteristics of the physical activity in the near past affect the progress of recovery by including the computation of separate downslope components for previous bouts of exercise and physical activity.

A BFI peak is defined as the value of BFI at time point wherein the current value of BFI is higher or equal to the previous value of BFI and the next value of BFI is lower than the current value of BFI. The value of each BFI peak is stored in the system.

In some point the effect of the prior peaks in BFI are no longer stored in the system or taken to consideration in the accumulation of increases in BFI. These incidents may be defined with a threshold value (e.g., preferably absolute quantity) or based on other criterion, such as the percentual distribution of the recovery.

In current embodiment the BFI peaks are ignored for the simplicity of the calculation. However they become important if more accuracy is required and the phenomenon is wanted to be described more precisely. With the current preferred embodiment the BFI is not affected by the history implying that the current value is only affected by the previous BFI current intensity and time between the measurements.

$$zmf(x, p_1, p_2) = \begin{cases} 1.0, & x \leq p_1 \\ 1.0 - 2.0 \cdot \left(\frac{x - p_1}{p_1 - p_2}\right)^2, & x > p_1 \wedge x \leq \frac{p_1 - p_2}{2} \\ 2.0 \cdot \left(\frac{p_2 - x}{p_1 - p_2}\right)^2, & x > \frac{p_1 - p_2}{2} \wedge x < p_2 \\ 0.0, & x \geq p_2 \end{cases} \qquad \text{Equation 3}$$

$$y_1(\Delta t, BFI_t) = downslope(\Delta t) \cdot BFI_t \qquad \text{Equation 4}$$

$$y_2(\Delta t, BFI_t, excercise\_intensity_t) = (1 - zmf(exercise\_intensity_t, p_1, p_2)) \cdot upslope(\Delta t, BFI_t) + $$
$$+ zmf(excercise\_intensity_t, p_1, p_2) \cdot y_1(\Delta t, BFI_t)$$

$$BFI_{t+1} = \max\{y_1(\Delta t, BFI_t), y_2(\Delta t, BFI_t, exercise\_intensity_t)\}$$

Figure 3:
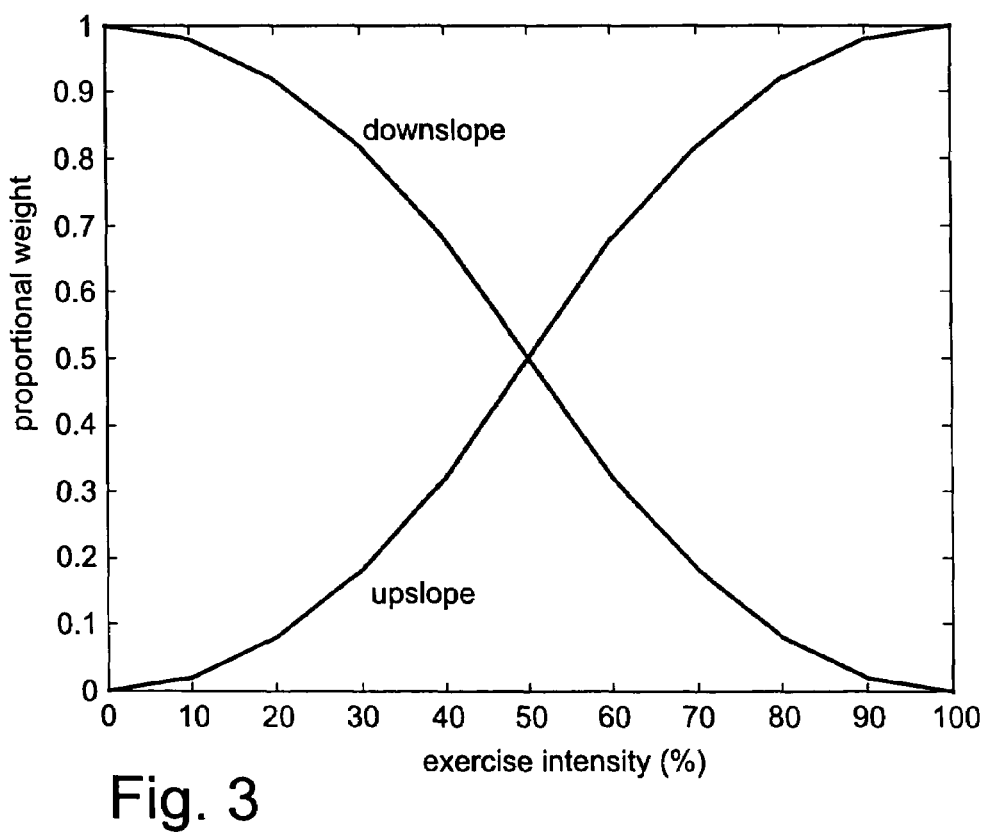
FIG. 3. The weight function to combine down- and upslope components as a function of exercise intensity.

The combination of the down- and upslope components is presented in Equation 4. The first function $y_1$ expresses the level BFI in the system. The second function $y_2$ gives a combination of the down- and upslope components as a weighted average where the weights are expressed as a function of exercise intensity. An example of the weights of the components determined as a function of exercise intensity is illustrated in FIG. 3 and Equation 3, where $p_1$ and $p_2$ are set zero and one respectively. The maximum of these functions is used as a new BFI.

The combination of upslope and downslope components provides the difference in the BFI from the previous value of the BFI. Correspondingly, the new level of BFI is obtained from summing the combination of upslope and downslope components with the previous value of the BFI. The BFI may be used as such, wherein it denotes the level of the predicted measure (e.g., the expected amount of additional $VO_2$ consumption during recovery) or as in proportional units, where the index is being referenced to preset or individual maximum values of body fatigue.

The use of the weighting functions is optional in combining the two upslope and downslope components, since the same weighting properties that are dependent on the exercise intensity can be also set into upslope and downslope components directly. For example, in the particular implementation of the upslope presented in Equation 1 the weighting of upslope in combination is optional since the exercise intensity based weighting can be included already in the calculation of upslope. However, the benefit of using the additional weighting of upslope and downslope components is in that it provides additional means of controlling the accumulation and decrease of BFI according to the physiological conditions and scale.

It is important to notice that this innovation may be also implemented without the separate downslope component, wherein the so-called upslope component would contain some of the properties of the downslope component, so that at low intensities of physical activity the change in BFI value would be negative and thus, BFI would decrease. This implementation might preferred in some contexts wherein the recovery of a particular physiological condition is relatively straightforward and may be presented as a continuum from maximal recovery to maximal increase.

Another implementation may be using only the upslope component to quantify an accumulative index of the desired physiological index during a condition wherein there is no recovery or recovery is not in the scope of measurement.

According to a yet another implementation, the information on the accumulative properties of the BFI may be used to form a pre-defined set of parameters that may be used to characterize the accumulative process of BFI. In this manner, for example, the present innovation and the presented embodiments may be used as a training set to another method. Another example would the use of the present innovation and embodiment to form a table that would include the accumulative accounts of the present innovation and could be referred to in terms of, for example, duration of exercise and intensity of exercise, and yet would give an estimate of BFI that would inherently include information on the accumulated value of BFI.

Figure 7A:
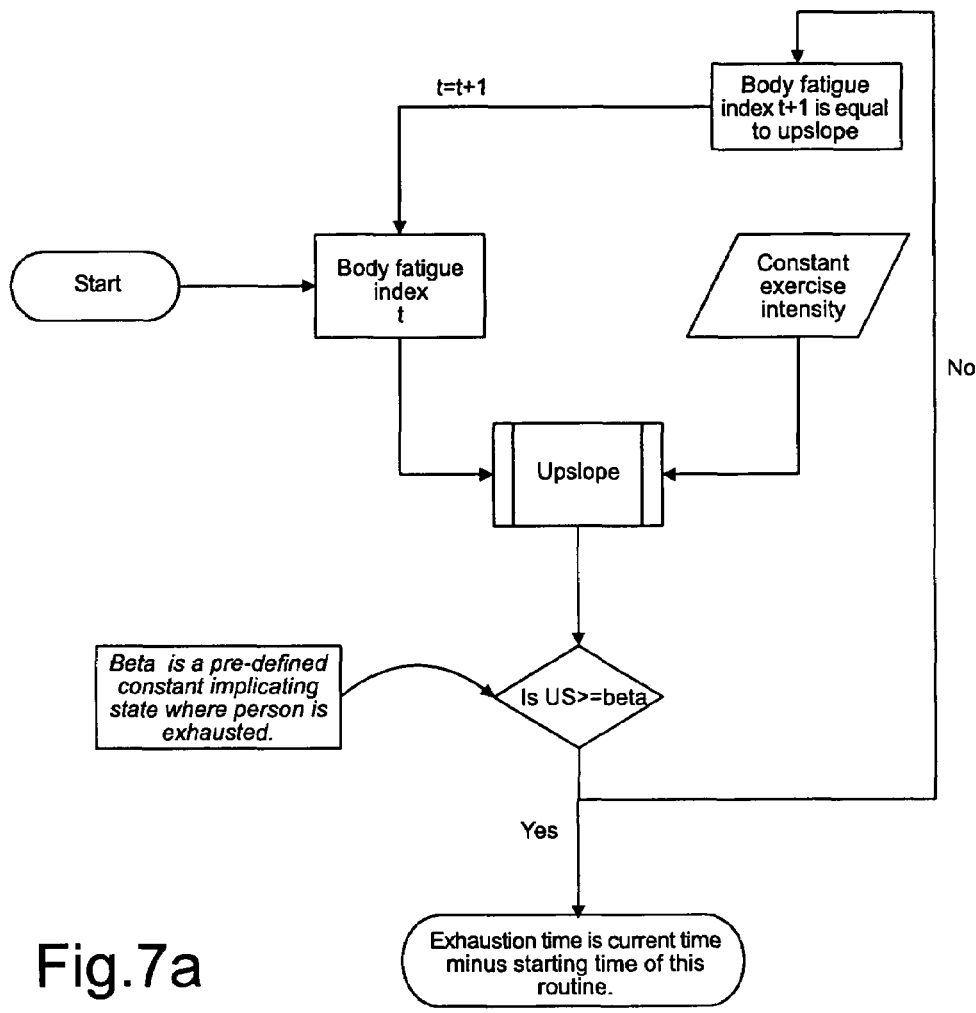
FIG. 7a. A flowchart presenting the modeling of time to exhaustion or other limit or target e.g., training effect.

Time to exhaustion refers to the estimated time (e.g., in minutes) that the user can engage within present level of exercise intensity before the occurrence of physical exhaustion. Time to exhaustion is an example of a preset upper limit that may be used to determine the time interval to a certain physiological condition or effect. Time to exhaustion is defined with a threshold value indicating the maximum possible body fatigue for the individual and with an inverse of the up-slope component indicating the time to reach the threshold with the chosen exercise intensity. FIG. 7a presents a flowchart illustrating the calculation of time to exhaustion. Another very useful preset limit would be training effect, that is, the time that is required to exercise at a given intensity to gain a certain training effect, where the upper limit for the gaining a particular training effect is determined by the accumulation of BFI that has been related to a physiological effect. Thus, for example, a limit for an improving training effect may be preset to a EPOC level of 250 ml/kg. In this case, it is especially fruitful to interpret the maximal value of BFI, which indicates the total integrated training effect of a particular training session.

Another very useful upper limit would be, for example, a level of BFI that would be optimal for energy consumption during low to medium intensity exercise. In this embodiment, the user could be also given information not only on the time that is required to gain the upper limit, but also information on whether the upper limit would be reached too early to gain optimal weight management results. In a similar manner, other embodiments are also possible in terms of gaining specific fitness effects and for the control of, for example, physical activity in elderly people or clinical condition wherein it is important to exercise within defined range.

One embodiment would integrate two or more measures of maximal values of BFI to form a longer-term information on the accumulated workload and fatigue of a training program. Thus, one might for example gain information that, when two or more maximal BFI values are combined, the training has been too hard or too low for a given period, say, week. This may potentiate a very useful training aid for persons that are willing to gain specific fitness effects by training. To give information on such conditions, the scaling of BFI may be defined according to the specific criteria of the training program (e.g., beginners program, marathon program) and physiological characteristics of the user (e.g., maximal oxygen consumption, $VO_{2max}$).

Figure 7B:
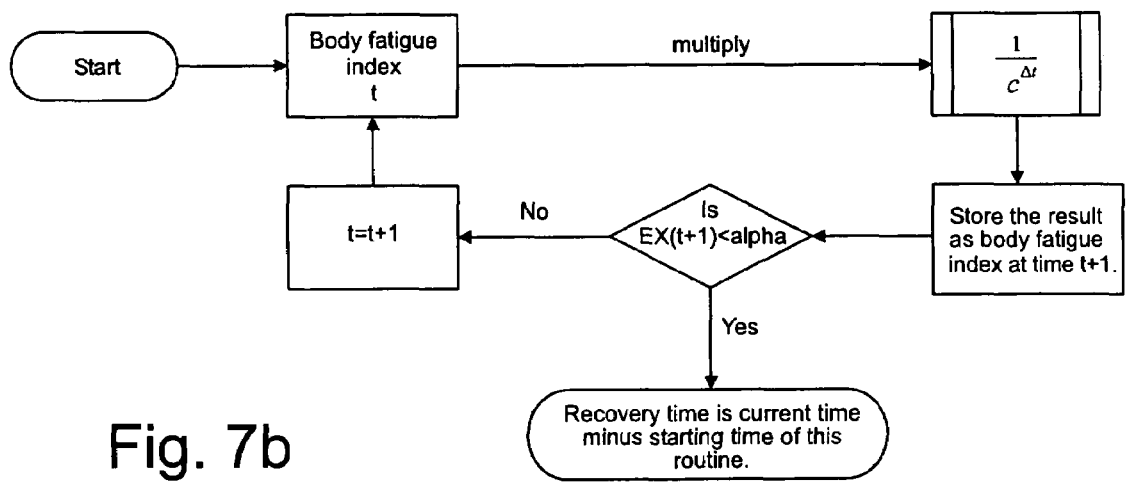
FIG. 7b. A flowchart presenting the modeling of time point of recovery or other limit.

Recovery time refers to the estimated time (e.g., in minutes) that will be taken for the user to perform acute recovery from the exercise, given that the user would begin recovery at the time instant. Recovery time is calculated from the inverse function of Equation 2 and recovery threshold, i.e. the time needed to reach the recovery threshold is estimated. The recovery history is used as before. FIG. 7b presents a flowchart illustrating the calculation of recovery times. In a similar manner to the upper limits described above, a preset limit may be set to any level characterizing physiological condition, which may be then used to determine the expected time period that is required until the pre-defined physiological condition is achieved. This information may be obtained both during the exercise and after the exercise.

The prediction of the recovery of the autonomic nervous system, in specific heart rate and heart rate variability, from exercise and physical activity related effects potentiates the monitoring of the progress of the actual recovery process. This may be achieved by applying, as a preferred embodiment, a comparison between observed heart rate level and predicted heart rate level. A higher heart rate level than that predicted indicates that recovery is progressing with a slower rate than that expected and, in a similar manner, a lower heart rate level than that predicted indicates that recovery is progressing with a faster rate than that expected. This procedure enables the production of information on the rate of recovery on the basis of comparing the observed level of heart rate to predicted level of heart rate. The advantage of this method is that it provides a method of evaluating the rate of recovery to the expected rate of recovery due to cumulated body fatigue, thus providing information on the progress of recovery from exercise as associated with the present state of the body.

It is well-known that, following exercise and physical activity, cardiovascular system and in particular heart beat level shows an increased level of activity. This poses a problem for the analysis of ambulatory heart beat signal, wherein it is of importance to differentiate physical activity induced autonomic nervous system reactivity from other sources of reactivity, such as, for example, physical or mental stress. As an application, and in accordance with the present innovation, BFI, shape of recovery (i.e., as determined by downslope component) and the predicted recovery levels of heart rate level and heart rate variability levels may be used to differentiate the effects of physical activity associated autonomic nervous system reactivity from other sources of reactivity. When using this application, a recovery function of heart rate and HRV based on empirical data similar to that as presented in FIG. 2 provides a model-based prediction for the recovery of heart rate level after exercise and potentiates a detection and differentiation of exercise induced reactivity from other sources of reactivity.

The level of predicted oxygen consumption during the recovery may be also used to correct the estimates of oxygen consumption and energy consumption that are based on the use of heart rate level or other input, since the level of heart rate may be provide accurate information on the oxygen consumption level and energy consumption level during recovery from exercise and physical activity. The BFI may be also useful in enhancing the accuracy of estimating oxygen consumption and energy consumption during different phases of exercise, since the relationship of, for example, heart rate to the oxygen consumption and energy consumption is different at the beginning of exercise and after some period of exercise. To summarize, given its accumulative and dynamic properties of the BFI, it can be used as a source of information on the phase and exercise dynamics in general to provide additional accuracy for the various methods of deriving information on oxygen consumption and energy consumption.

Figure 8A:
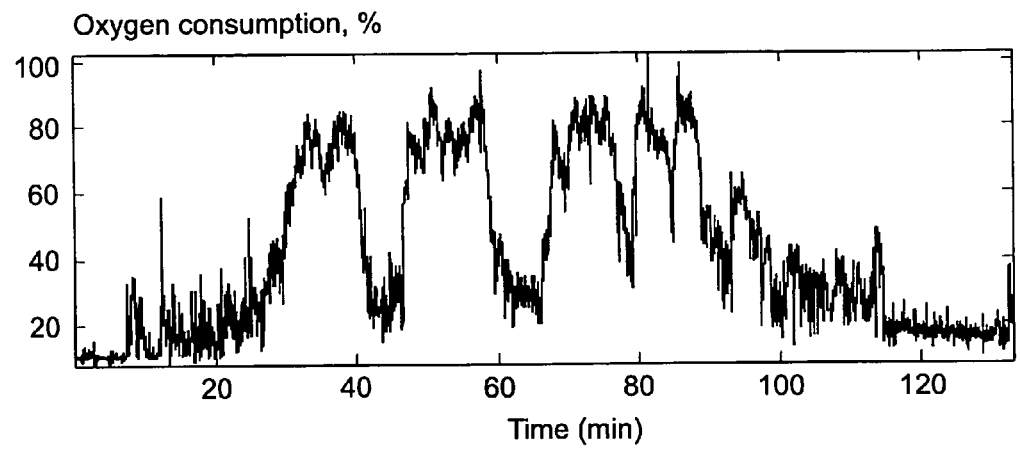
FIG. 8. An example of oxygen consumption measurement that is scaled in proportion to maximal oxygen consumption (8a) and BFI (8b) during exercise.
Figure 8B:
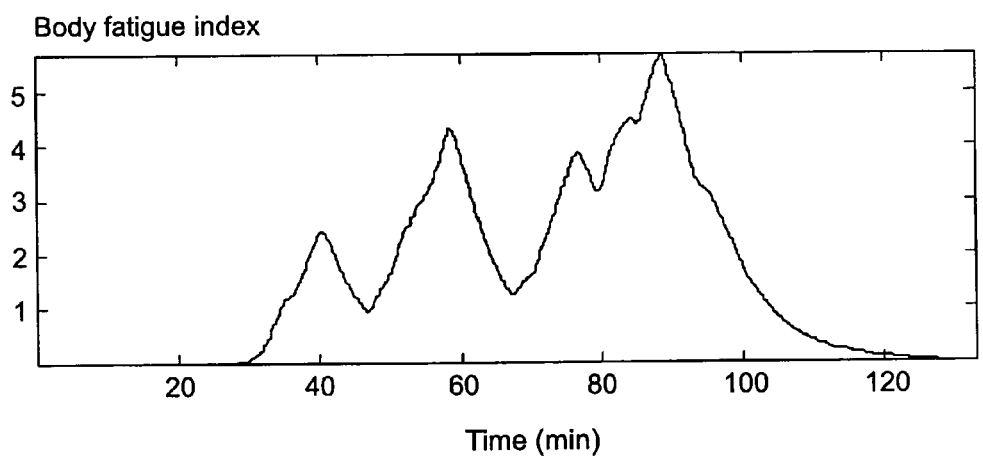

In FIG. 8 there is the input signal of physical activity (oxygen consumption) corresponding to BFI presented in FIG. 8b. Recovery periods of BFI are well seen between exercise periods. Scaling is arbitrary.

Figure 9:
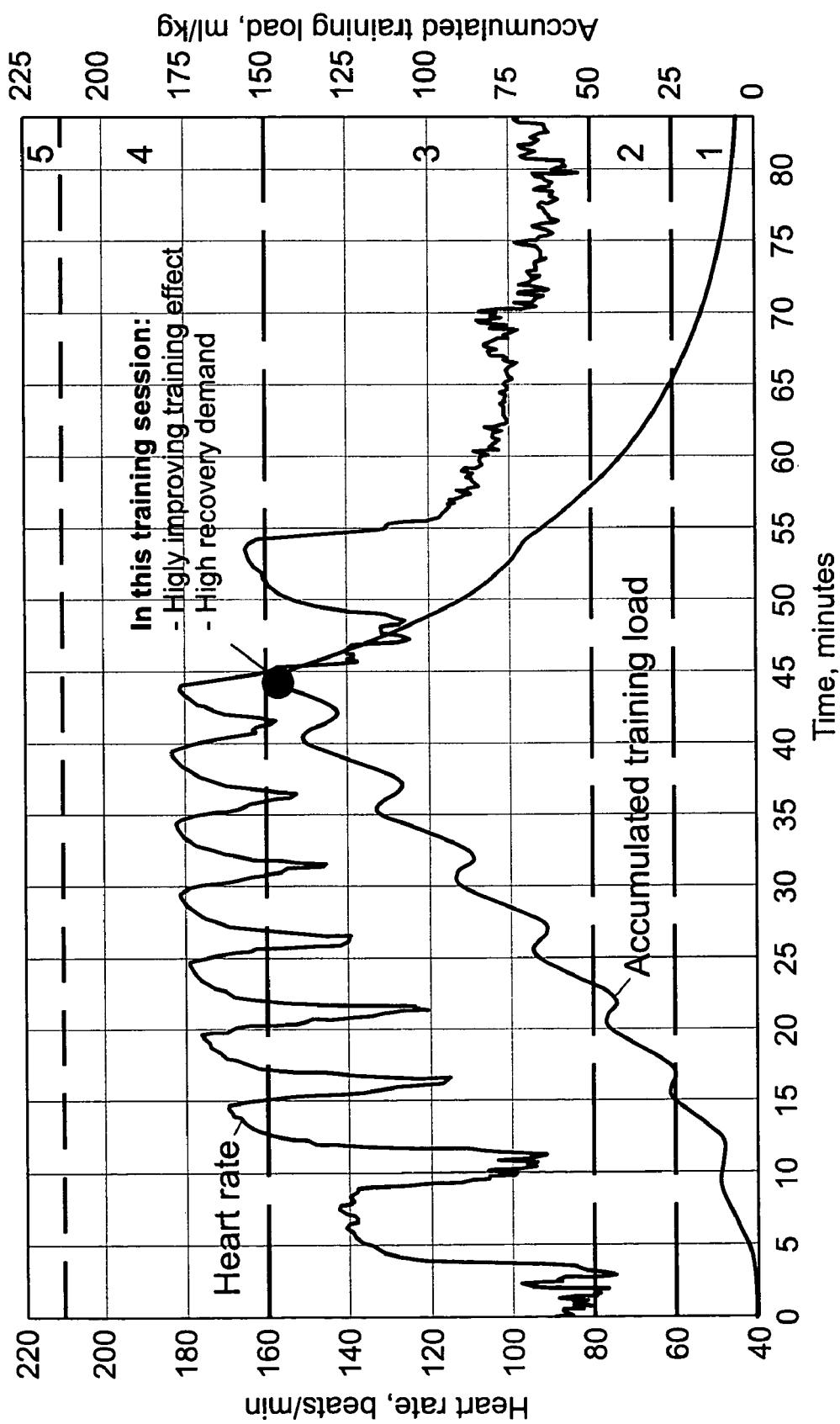
FIG. 9. An example of the use of the modeling of fatigue.

An example of the use of the modeling of fatigue is presented in FIG. 9. Accumulated training load as measured in the quantity of exercise-post oxygen consumption (EPOC, which is also often referred to as oxygen debt), that is, the extent of additional oxygen consumption after exercise (as expressed here in ml/kg), in the context of interpreting and predicting training effect and recovery demand are shown during exercise. In this particular example the limits of the training effect are set as reflecting temporal length and intensity of exercise that is required to gain a certain amount of EPOC inducing a particular training effect. In this figure, based on the amount of EPOC, there are five different predetermined zones of training effects: (1) No training effect, (2) Minor (maintaining) training effect, (3) Improving training effect, (4) Highly improving training effect, and (5) Overreaching training effect. It is of note here that a particular level of fatigue and recovery demand is associated with each zone of training effect, recovery need being highest in zone 5. It should be in particular noted that the limits may be set according to user's background characteristics (e.g., fitness level, sex, training background) and according to specific aims (e.g., to loose weight, gain fitness effects and endurance).

Figure 10:
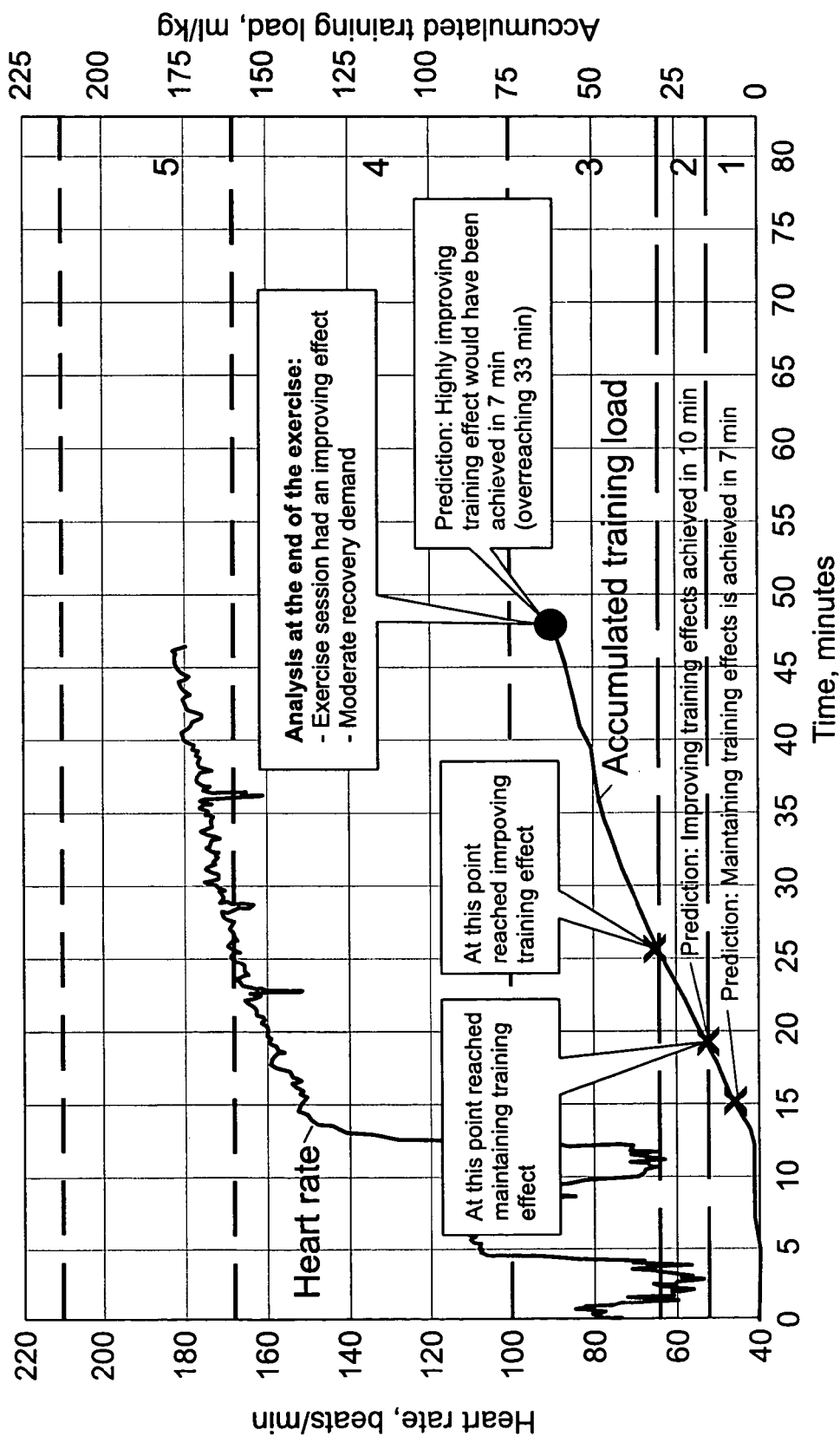
FIG. 10. An example of the real-time determination of the training effect on the basis of accumulated training load and fatigue accumulation.

An example of the real-time determination of the training effect on the basis of accumulated training load and fatigue accumulation is shown in FIG. 10. This should be interpreted in a Similar manner to FIG. 9.

Implementations of the invention can be a computer software in a personal computer, a heart rate monitor (wrist top computer), ECG-monitoring or pulse monitoring equipment such as a cardiac pace maker and an ergometer (a stationary bicycle) or other fitness exercise equipment. Generally an implementation consists of a processing unit, a terminal, software and at least one input device.

The invention claimed is:

1. Method for providing an index (BFI) depicting a person's accumulated body fatigue, the method comprising the steps of:
   measuring the person's intensity of physical activity through one or more parameters from the measurement of one or more signals obtained sequentially as input, said parameters being information on the intensity of the person's physical activity;
   setting a predetermined initial value to the index (BFI);
   calculating an upslope component and an downslope component of the index (BFI) determined with said parameters;
   calculating a combination of the upslope and the downslope components;
   calculating each next value of the index (BFI) as a sum of the previous value of the index (BFI) and a difference formed from said combination;
   wherein the upslope component and the downslope component are each calculated according to a function, which is scaled by a preset physiological character.

2. Method according to claim 1, characterized in that the function is independent from the duration of the physical activity.

3. Method according to claim 1, characterized in that the preset physiological character relates to an accumulated value, which is a function of quantity of body requirements for recovery after exercise and physical activity.

4. Method according to claim 1, characterized in that the preset physiological character relates to an accumulated value, which is a function of a training effect.

5. Method according to claim 1, characterized in that the downslope component of the index (BFI) estimates recovery and decrease in the index (BFI) with decreasing physical activity.

6. Method according to claim 1, characterized in that it is determined a prediction of the time interval after which the user engaged in physical activity is expected to attain a preset limit due to accumulation of body fatigue that is induced by continuing physical activity in the chosen intensity.

7. Method according to claim 1, characterized in that it is determined by the prediction of the time interval requirements for recovery after the physical activity.

8. Method according to claim 1, characterized in that information on the increased heart beat level during recovery is determined.

9. Method according to claim 1, characterized in that the wherein information on the level and recovery of oxygen consumption is used to enhance the accuracy of oxygen consumption or energy consumption estimation during recovery from the physical activity.

10. Method according to claim 1, characterized in that information on the level of the index (BFI) is used in the estimation of oxygen consumption or energy consumption level in addition to other method.

11. Method according to claim 5, characterized in that the predicted downslope component of heart rate or heart rate variability is used as a reference value to determine information on the process of recovering from physical activity.

12. Method according to claim 1, characterized in that the method is used in a wearable computer.

13. Method according to claim 1, characterized in that the method is used in a fitness exercise equipment.

14. Method according to claim 1, characterized in that the method is used in a PC-software.

15. Method according to claim 1, characterized in that the method is used in ECG/pulse-monitoring equipment.

16. Method according to claim 1, characterized in that the BFI is indexed as a function of exercise time and exercise intensity.

17. Method according to claim 1, characterized in that an intermediate measure reflecting accumulative physical activity is used in the calculation instead of the index (BFI), which measure is then transferred to value of the index (BFI).

* * * * *